US006551248B2

United States Patent
Miller (10) Patent No.: US 6,551,248 B2
(45) Date of Patent: Apr. 22, 2003

(54) SYSTEM FOR ATTACHING AN ACOUSTIC ELEMENT TO AN INTEGRATED CIRCUIT

(75) Inventor: David G. Miller, North Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 36 days.

(21) Appl. No.: 09/919,470

(22) Filed: Jul. 31, 2001

(65) Prior Publication Data

US 2003/0028108 A1 Feb. 6, 2003

(51) Int. Cl.⁷ .................................................. A61B 8/06
(52) U.S. Cl. ........................ 600/459; 29/25.35; 310/334
(58) Field of Search ............................. 600/459; 310/334, 310/336; 29/25.35

(56) References Cited

U.S. PATENT DOCUMENTS 5,435,313 A * 7/1995 Noda et al. ................. 600/459
5,744,898 A * 4/1998 Smith et al. ................ 310/334

* cited by examiner

Primary Examiner—Marvin M. Lateef
Assistant Examiner—Ruby Jain
(74) Attorney, Agent, or Firm—John Vodopia (57) ABSTRACT

A system for attaching an acoustic element to an integrated circuit includes various ways in which to connect piezoelectric ceramic or micro-machined ultrasonic transducer (MUT) elements to an integrated circuit (IC), thus reducing the number of conductors required to connect the acoustic element to the IC by combining the signals in the IC. In another aspect of the invention, the transducer elements include an electrically conductive acoustic layer comprising a backing layer and/or a de-matching layer that is connected to an IC.

45 Claims, 9 Drawing Sheets

SYSTEM FOR ATTACHING AN ACOUSTIC ELEMENT TO AN INTEGRATED CIRCUIT

TECHNICAL FIELD

The present invention relates generally to ultrasonic transducers, and, more particularly, to a system for attaching the acoustic element of an ultrasonic transducer to an integrated circuit.

BACKGROUND OF THE INVENTION

Ultrasonic transducers have been available for quite some time and are particularly useful for non-invasive medical diagnostic imaging. Ultrasonic transducers are typically formed of either piezoelectric elements or micro-machined ultrasonic transducer (MUT) elements. The piezoelectric elements typically are made of a piezoelectric ceramic such as lead zirconate titanate (commonly referred to as PZT), with a plurality of elements being arranged to form a transducer assembly. A MUT is formed using known semiconductor manufacturing techniques resulting in a capacitive ultrasonic transducer cell that comprises, in essence, a flexible membrane supported around its edges over a silicon substrate. By applying contact material, in the form of electrodes, to the membrane, or a portion of the membrane, and to the base of the cavity in the silicon substrate, and then by applying appropriate voltage signals to the electrodes, the MUT may be energized such that an appropriate ultrasonic wave is produced. Similarly, when electrically biased, the membrane of the MUT may be used to receive ultrasonic signals by capturing reflected ultrasonic energy and transforming that energy into movement of the electrically biased membrane, which then generates a receive signal The transducer elements can be combined with control circuitry forming a transducer assembly, which is then further assembled into a housing possibly including additional control electronics, in the form of electronic circuit boards, the combination of which forms an ultrasonic probe. This ultrasonic probe, which may include various acoustic matching layers, backing layers, and dematching layers, may then be used to send and receive ultrasonic signals through body tissue.

In the past, joining an acoustic sensor, such as a piezoelectric ceramic transducer element or a MUT element, to the electrical control circuitry required the use of many individual wires to connect each element of the transducer array to the control circuitry. In the case of large transducer arrays having many hundreds or thousands of elements, large wiring harnesses were required. Unfortunately, a large wiring harness increases the bulk and cost of the ultrasonic probe. For ultrasonic probes designed to be used inside the human body, it is desirable to reduce the overall size of the ultrasonic probe and cable. One manner of reducing the size of the probe is to provide the transducer element control electronics on an integrated circuit (IC) assembly. An IC in proximity to the transducer array may be used to transmit and receive from many small transducer elements and may also be used to combine the signals, thereby reducing or eliminating the bulky and expensive cables that typically connect the ultrasonic probe elements to the control electronics.

Placing the transducer array over the IC results in greater packaging efficiency. Unfortunately, there is no convenient way to connect the piezoelectric ceramic or MUT transducer elements to the control electronics.

Therefore, it would be desirable to have a way in which to connect both the piezoelectric ceramic and MUT elements of an ultrasonic transducer array directly to an IC.

SUMMARY

The invention is a system for attaching an acoustic element to an integrated circuit (IC). The system provides various ways to connect piezoelectric ceramic or MUT transducer elements to an IC, thus reducing the number of conductors required to connect each element of the transducer array to the IC by combining the signals in the IC. In another aspect of the invention, the transducer elements include an electrically conductive acoustic layer having a backing layer and/or a dematching layer that is connected to an IC.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE INVENTION

The invention to be described hereafter is applicable to piezoelectric ceramic and micro-machined ultrasonic transducer (MUT) elements connected to an integrated circuit (IC).

Figure 1:
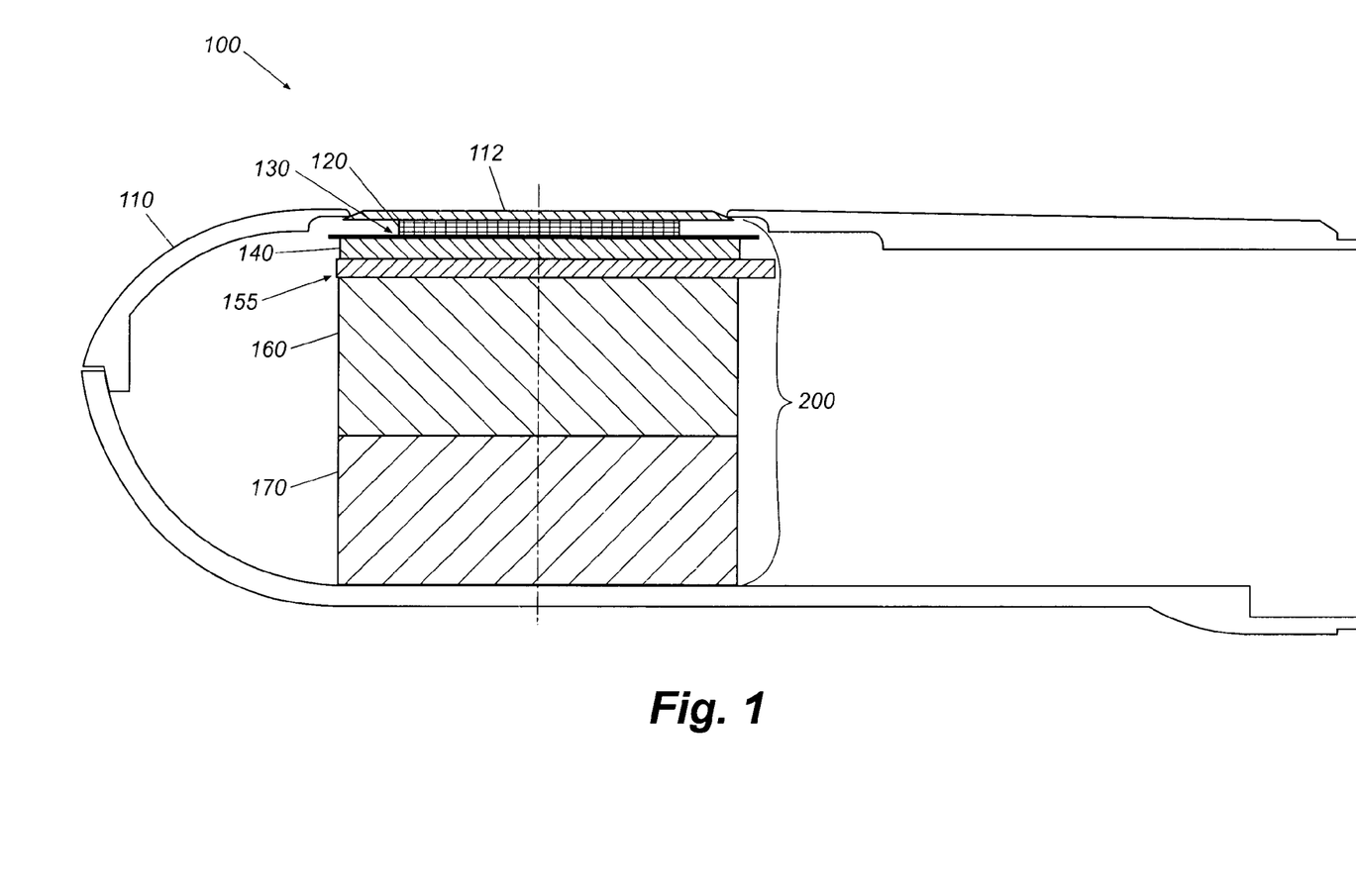
FIG. 1 is a cross-sectional schematic view of a transesophageal (TEE) ultrasonic probe.

FIG. 1 is a cross-sectional schematic view of a transesophageal (TEE) ultrasonic probe 100. The ultrasonic probe 100 includes a probe housing 110 that contains an ultrasonic transducer. The ultrasonic transducer includes an acoustic sensor 120 commonly comprising a number of transducer array elements (to be described in further detail below). The transducer elements may be piezoelectric ceramic or micro-machined ultrasonic transducer (MUT) elements. An acoustic window 112, through which ultrasonic energy is both transmitted from and received by the ultrasonic probe 100, is located along a surface of the probe housing 110 and in front of the acoustic sensor 120.

The acoustic sensor 120 is joined to an integrated circuit (IC) 140 through an interface 130. The interface 130 includes a redistribution layer 145 (shown and described in FIG. 2) applied over the active circuitry of the integrated circuit 140. The active circuitry of the IC 140 can be formed on the surface of a suitable substrate (150 of FIG. 2) and is typically fabricated over a silicon (Si) substrate. However, other semiconductor substrate materials may be used to fabricate the IC 140. The IC substrate is bonded to a circuit board 155 having acoustic impedance that matches the acoustic impedance of the IC substrate. The circuit board 155 is bonded to a backing material 160 by thin bonds to prevent acoustic reflections from the bonded surfaces.

The acoustic sensor 120 typically includes many hundreds or thousands of transducer elements, and preferably includes 2500 ultrasonic elements. Each of the elements requires an electrical connection to the electronic control circuitry (not shown) associated with the ultrasonic probe 100. The IC 140 allows many such electrical connections to be combined, thereby reducing the number of individual connections within the ultrasonic probe 100.

Typically, an acoustic backing 160 is applied behind the circuit board 155 in order to absorb any ultrasonic energy that migrates through the circuit board 155. A heat sink 170 is applied behind the acoustic backing 160 in order to remove heat from the acoustic sensor 120 and the IC 140. The acoustic sensor 120, interface 130, IC 140, circuit board 155, acoustic backing 160 and heat sink 170 comprise an ultrasonic transducer 200.

Figure 2:
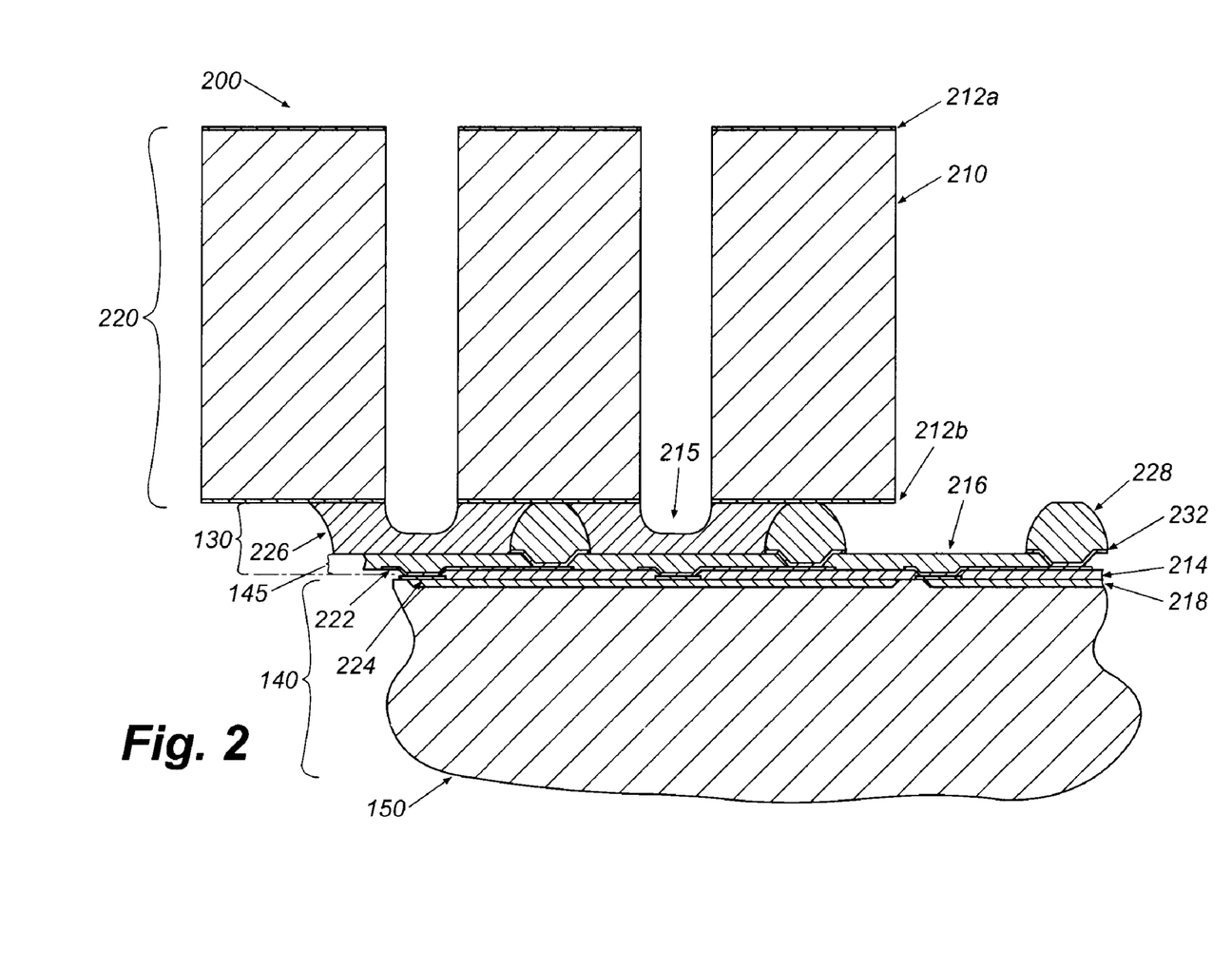
FIG. 2 is a cross-sectional schematic view illustrating a portion of the ultrasonic transducer of FIG. 1.

FIG. 2 is a cross-sectional schematic view illustrating a portion of the ultrasonic transducer 200 of FIG. 1. Although omitted from the ultrasonic transducer 200 of FIG. 2, there is commonly a circuit board (155 of FIG. 1), an acoustic backing 160 and heat sink 170 (as shown in FIG. 1) associated with the ultrasonic transducer 200. Furthermore, matching and dematching layers are omitted for clarity.

The ultrasonic transducer 200 includes an acoustic sensor 220 that, in this embodiment, comprises a plurality of piezoelectric ceramic transducer elements, an exemplar one of which is illustrated using reference numeral 210. A plurality of piezoelectric ceramic transducer elements 210 are arranged in an array, which typically includes many hundreds or thousands of individual transducer elements, and in a preferred embodiment, includes 2500 elements. Each piezoelectric ceramic transducer element 210 includes an element metalization layer 212a applied to the upper surface as shown. The element metalization layer 212a provides an electrical ground connection for each element 210. The ground connection typically includes a conductor (not shown) connecting each element 210 to a suitable electrical ground. In accordance with an aspect of the invention, each piezoelectric ceramic transducer element 210 is joined to the active circuitry 218 associated with IC 140 through a redistribution layer 145. The redistribution layer 145 can be applied over the active circuitry 218, the IC pads, an exemplar one of which is illustrated using reference numeral 224, and the die passivation layer 214 located on the IC 140. The IC substrate 150 and the active circuitry 218 comprise the IC 140. The die passivation layer 214 is applied over the active circuitry 218 and the IC pads 224, leaving the IC pads 224 exposed.

The redistribution layer 145 includes a number of redistribution conductors, an exemplar one of which is shown using reference numeral 222, in contact with portions of the active circuitry 218 through the IC pads 224. The redistribution layer 145 also includes a secondary passivation layer 216 applied over the redistribution conductors 222 and the die passivation layer 214. The redistribution conductors 222 redistribute the connections of the active circuitry 218, through the IC pads 224, to appropriate locations corresponding to each piezoelectric ceramic transducer element 210. The redistribution conductor 222 is a conductive material that connects each IC pad 224 to a respective metal contact 232, and can be formed using fine trace IC technology. Each metal contact 232 corresponds to a piezoelectric ceramic transducer element 210.

The die passivation layer 214 and the secondary passivation layer 216 can be formed of, for example, but not limited to, silicon dioxide or polymer. The redistribution layer 145 aids in reducing capacitive coupling between the active circuitry 218 and the transducer elements 210. An additional passivation layer (not shown) can be applied between the die passivation layer 214 and the redistribution conductors 222 to further reduce capacitive coupling between the active circuitry 218 and the transducer elements 210, and is applicable to the other embodiments discussed. Furthermore, the secondary passivation layer 216 aids in leveling the uneven surface resulting from the formation of the active circuitry 218 over the IC substrate 150.

In one embodiment, each piezoelectric ceramic transducer element 210 is joined to a respective metal contact 232 using a conductive element 228. The conductive element 228 can be, for example, a solder ball, or bump, that forms an electrical contact between the metal contact 232 and an element metalization layer 212b applied to the underside of each piezoelectric ceramic transducer element 210. In this manner, electrical contact between the piezoelectric ceramic transducer element 210 and the active circuitry 218 is achieved. Although illustrated in FIG. 2 using solder bumps as the conductive element 228, a variety of other techniques are available for electrically connecting the metal contact 232 to the element metalization layer 212b of each piezoelectric ceramic transducer element 210. For example, instead of solder bumps, gold bumps can be used. Further, conductive adhesive or conductive polymer bumps can be used to connect the metal contact 232 to the element metalization layer 212b. Further still, as will be described below with respect to FIG. 4, a technique known as "thin-line bonding" can be used to connect the element metalization layer 212b directly to the metal contact 232 resulting in a direct ohmic connection. In such an embodiment, the surface of the secondary passivation layer 216 and the metal contact 232 can optionally be lapped flat, or planarized, to level the surface of the redistribution layer 145 and of the integrated circuit 140, prior to thin-line bonding the element metalization layer 212b to the metal contact 232.

Adhesive material 226 fills the gaps between each conductive element 228 and the space between each piezoelectric ceramic transducer element 210 and the secondary passivation layer 216. The adhesive 226 is typically non-conductive and can be a variety of adhesives such as, for example but not limited to, epoxy. The adhesive 226 can also function as a dematching material, which acts as an acoustic reflector.

The ultrasonic transducer 200 is typically constructed by forming the secondary passivation layer 216 and the metal contacts 232 over the active circuitry 218 of the IC 140. The conductive elements 228 are then deposited over the metal contacts 232. The adhesive 226 is then deposited and the material from which the transducer elements 210 are formed is bonded to the secondary passivation layer 216, resulting in an electrical connection between the element metalization layer 212b and the conductive elements 228. The transducer elements 210 are then formed by removing a portion of the material that forms the transducer elements 210 and the element metalization layers 212a and 212b. For example, the transducer elements 210 can be cut using a dicing saw stopping before the saw contacts the metalization layer 212b. The remaining material of the transducer elements 210 and the metalization layer 212b can then be removed by, for example, burning with a laser. The resulting saw kerf 215 creates the independent transducer elements 210 and removes the electrical connection between transducer elements 210.

Figure 3:
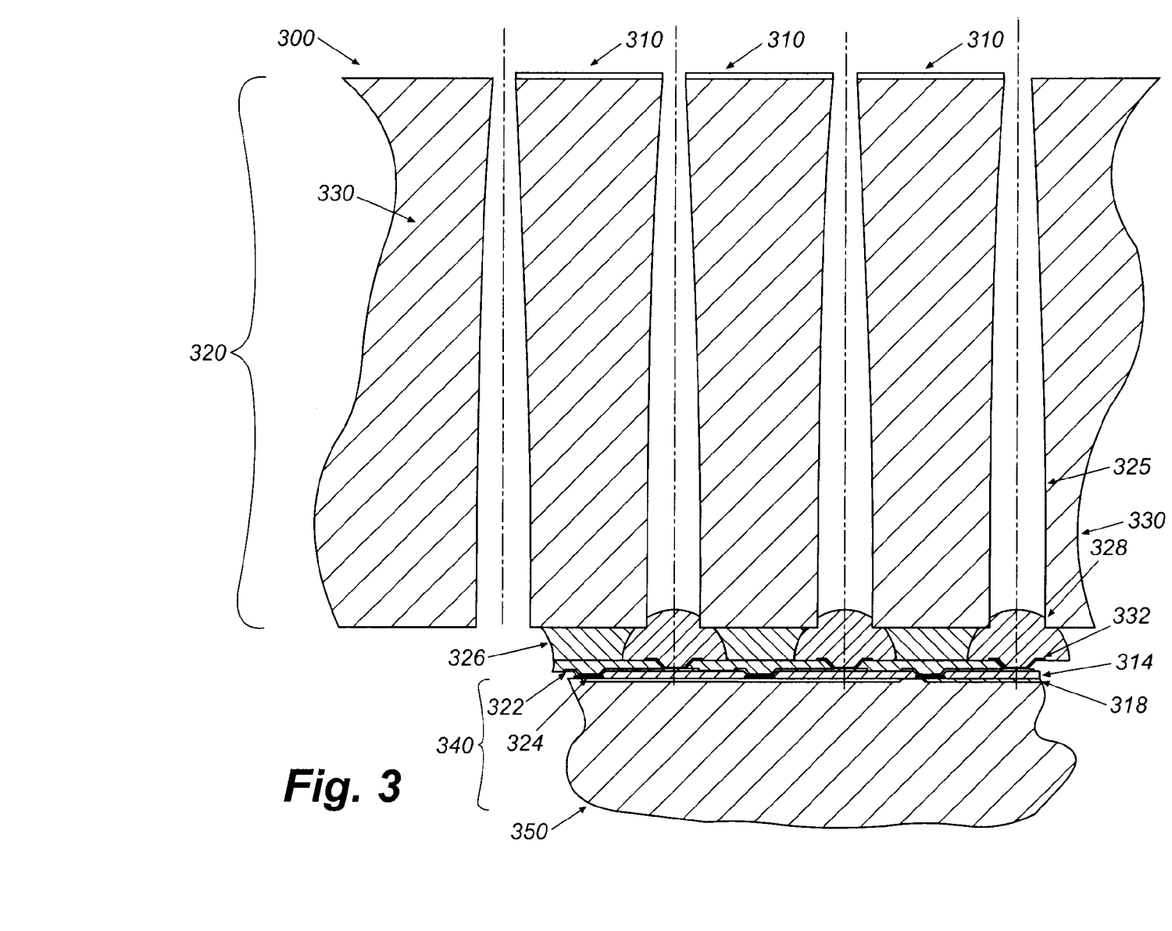
FIG. 3 is a cross-sectional schematic view of an alternative embodiment of the ultrasonic transducer of FIG. 2.

FIG. 3 is a cross-sectional schematic view of an alternative embodiment of the ultrasonic transducer 200 of FIG. 2. The ultrasonic transducer 300 of FIG. 3 includes an acoustic sensor 320 comprising a plurality of MUT elements 310. The MUT elements 310 are formed on a MUT substrate 330. Each MUT element 310 includes one or more MUT cells (not shown). If more than one MUT cell is used to form the MUT element 310, the MUT cells forming the MUT element typically are commonly connected. As known to those having ordinary skill in the art, MUT elements 310 can be fabricated on a substrate 330, such as silicon, using semiconductor device processing technology. Each MUT element 310 includes an electrical ground connection (not shown) typically extending over the surface of each MUT element 310. The ground connection typically includes a conductor (not shown) connecting each MUT element 310 to a suitable electrical ground.

In accordance with an aspect of the invention, each MUT element 310 includes one or more small diameter holes, referred to as vias, an exemplar one of which is illustrated using reference numeral 325. The via 325 extends through the MUT substrate 330 and makes contact with each MUT element 310. Each via 325 is doped so as to be electrically conductive, thereby providing an electrical connection to each MUT element 310. In accordance with this aspect of the invention, each MUT element 310 is located adjacent to a via 325. Each via 325 extends through the MUT substrate 330 and contacts one of the conductive elements 328. In this manner, the conductive via 325 electrically couples the MUT element 310 to the conductive element 328. It should be noted that all the alternative conductive elements mentioned above in FIG. 2 apply to FIG. 3. Each conductive element 328 makes contact with a respective metal contact 332. Each metal contact 332 makes electrical contact with a respective redistribution conductor 322, which in turn makes electrical contact with a respective IC pad 324. Each IC pad 324 contacts a portion of the active circuitry 318. In this manner, the active circuitry 318 located on the IC 340 makes electrical contact, through the redistribution conductors 322, to the conductive elements 328 and to each MUT element 310. Adhesive material 326 fills the gaps between each conductive element 328 and the space between the MUT substrate 330 and the secondary passivation layer 316. The adhesive 326 is typically non-conductive and similar to the adhesive 226 described above.

Figure 4:
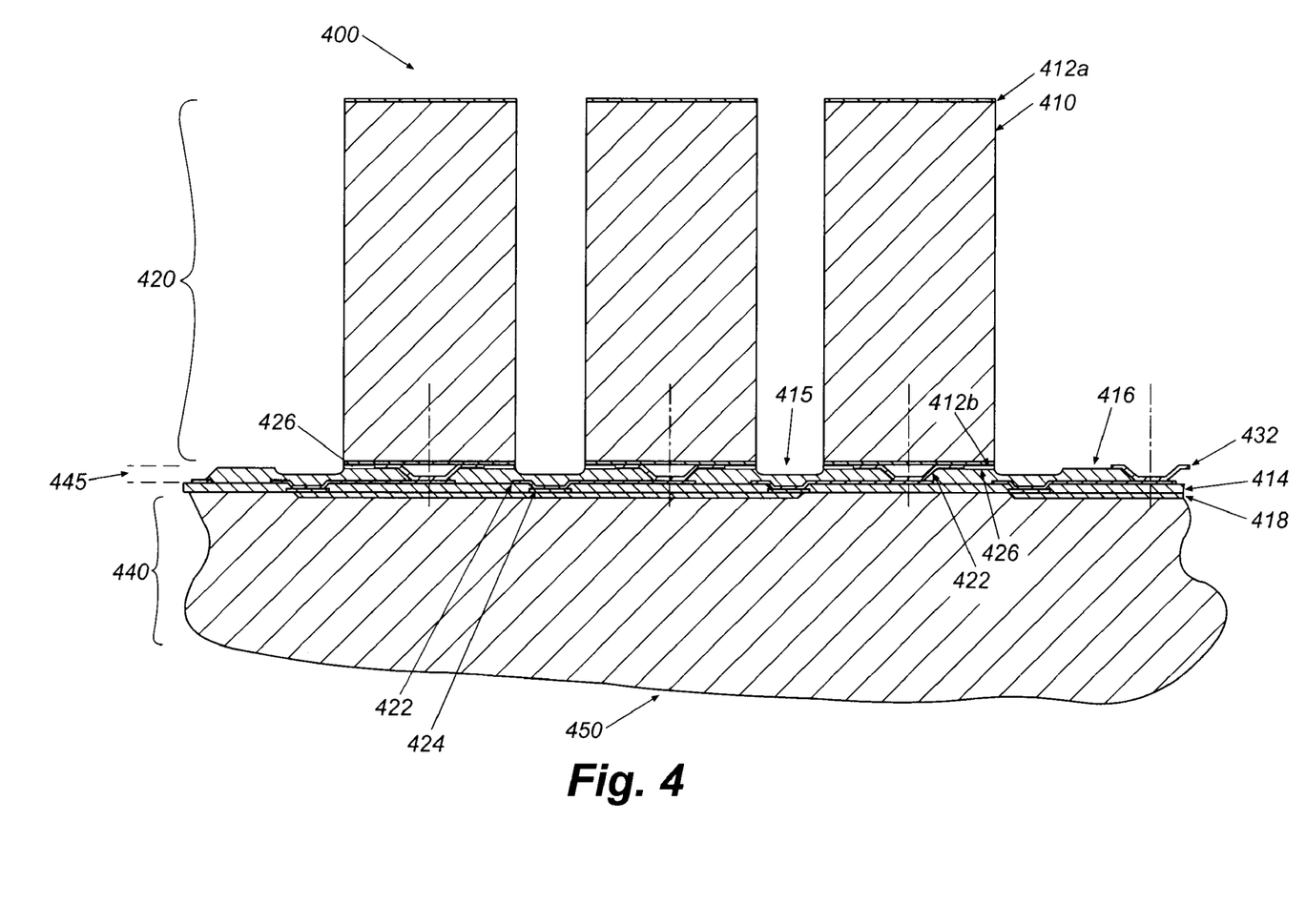
FIG. 4 is a cross-sectional schematic view illustrating another alternative embodiment of the ultrasonic transducer of FIG. 2.

FIG. 4 is a cross-sectional schematic view illustrating another alternative embodiment of the ultrasonic transducer 200 of FIG. 2. The ultrasonic transducer 400 of FIG. 4 includes acoustic sensor 420, which in this example includes a plurality of piezoelectric ceramic transducer elements, an exemplar one of which is illustrated using reference numeral 410. Each piezoelectric ceramic transducer element 410 includes an element metalization layer 212a applied to the upper surface as shown. The element metalization layer 212a provides an electrical ground connection for each element 410. The ground connection typically includes a conductor (not shown) connecting each element 410 to a suitable electrical ground. Each piezoelectric ceramic transducer element 410 also includes an element metalization layer 412b applied to the underside as shown. The element metalization layer 412b allows direct electrical contact to be made between the piezoelectric ceramic transducer element 410 and the metal contact 432. As mentioned above, such a connection is typically referred to as a "thin-line bond." The thin-line bond uses an adhesive polymer material to mechanically connect the metal contact 432 directly to the exposed surface of the element metalization layer 412b of the piezoelectric ceramic transducer element 410. The thin-line bond is achieved because of the microscopic surface roughness that exists on the exposed surface of the element metalization layer 412b and the metal contact 432. This microscopic surface roughness provides a direct ohmic connection between the metal contact 432 and the element metalization layer 412b. The metal contact 432 is connected through the redistribution conductor 422 to the IC pad 424. The IC pad 424 connects to the active circuitry 418 located on the IC 440. The redistribution layer 445 includes the redistribution conductors 422 and a secondary passivation layer 416, which is similar to the secondary passivation layer 216, described above.

Similar to the ultrasonic transducer 200 of FIG. 2, the ultrasonic transducer 400 is typically constructed by forming the secondary passivation layer 416 and the metal contacts 432 over the active circuitry 418 and IC pads 424 of the IC 440. The exposed surface of the secondary passivation layer 416 and portions of the metal contacts 432 can then be lapped, or planarized, flat.

The adhesive 426 is then deposited and the material from which the transducer elements 410 are formed is bonded to the secondary passivation layer 416, resulting in a thin-line bond electrical connection between the element metalization layer 412b and the metal contacts 432. The transducer elements 410 are then formed by removing a portion of the material that forms the transducer elements 410 and the element metalization layers 412a and 412b. As described above, the transducer elements 410 can be cut using a dicing saw stopping before the saw contacts the metalization layer 412b. The remaining material of the transducer elements 410 and the metalization layer 412b can then be removed using, for example, a laser. The resulting saw kerf 415 creates the independent transducer elements 410 and removes the electrical connection between transducer elements 410.

Figure 5A:
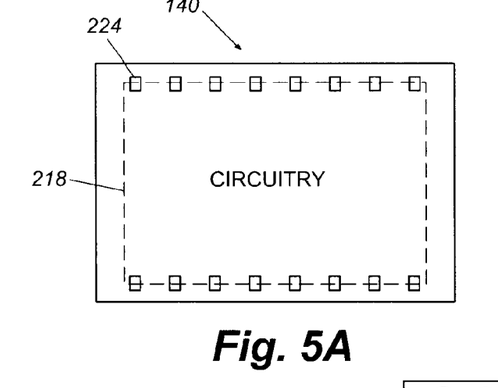
FIG. 5A is a plan view illustrating the IC in the ultrasonic transducer of FIG. 2.

FIG. 5A is a plan view illustrating the IC 140 of FIG. 2. The IC 140 includes a plurality of IC pads, an exemplar one of which is illustrated using reference numeral 224. The IC pad 224 connects to the active circuitry 218 and corresponds to the IC pad 224 of FIG. 2.

Figure 5B:
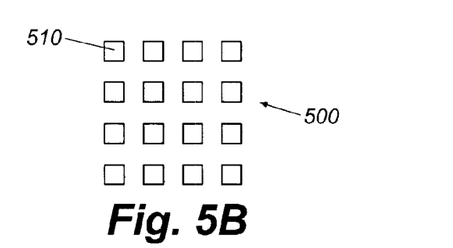
FIG. 5B is a plan view illustrating a footprint of a two-dimensional (2D) acoustic sensor.

FIG. 5B is a plan view illustrating a footprint of a two-dimensional (2D) acoustic sensor 500. For simplicity, the transducer array footprint 500 illustrates 16 transducer elements, an exemplar one of which is illustrated using reference numeral 510, arranged in a 4×4 array. However, a typical transducer array includes many hundreds or thousands of transducer elements.

Figure 5C:
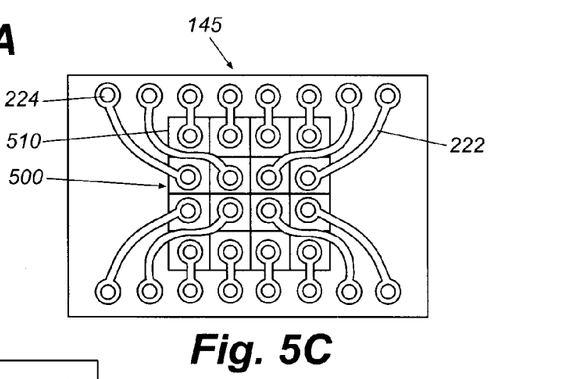
FIG. 5C is a plan view illustrating the redistribution layer of FIG. 2 including the transducer array footprint of FIG. 5B.

FIG. 5C is a plan view illustrating the redistribution layer 145 of FIG. 2 including the transducer array footprint 510 of FIG. 5B shown using a dashed line. Each redistribution conductor 222 connects one of the IC pads 224 to one of the pads 510 of the transducer array footprint 500. The redistribution conductors 222 in the redistribution layer 145 make electrical connections between the IC pads 224 and each respective transducer array element 510. Accordingly, both the transducer array footprint 500 and the design of the active circuitry 218 can be independently optimized and each transducer array element 510 connected to the appropriate portion of the active circuitry 218.

Figure 6A:
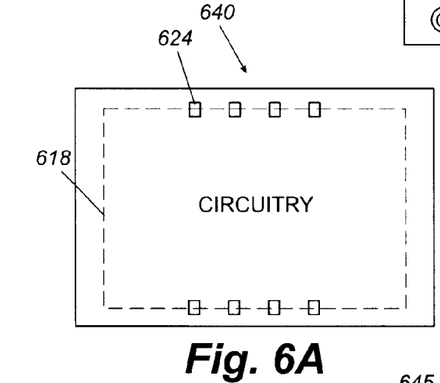
FIG. 6A is a plan view illustrating an alternative embodiment of the IC of FIG. 5A.

FIG. 6A is a plan view illustrating an alternative embodiment of the IC of FIG. 5A. The IC 640 includes a plurality of IC pads, an exemplar one of which is illustrated using reference numeral 624. The IC pad 624 connects to the active circuitry 618.

Figure 6B:
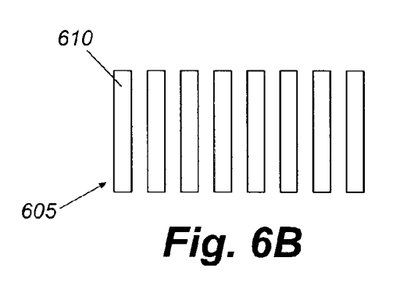
FIG. 6B is a plan view illustrating a footprint of a one-dimensional (1D) acoustic sensor.

FIG. 6B is a plan view illustrating a footprint of a one-dimensional (1D) acoustic sensor 605. The transducer array footprint 605 includes a plurality of transducer elements, an exemplar one of which is illustrated using reference numeral 610, arranged in a 1×8 array.

Figure 6C:
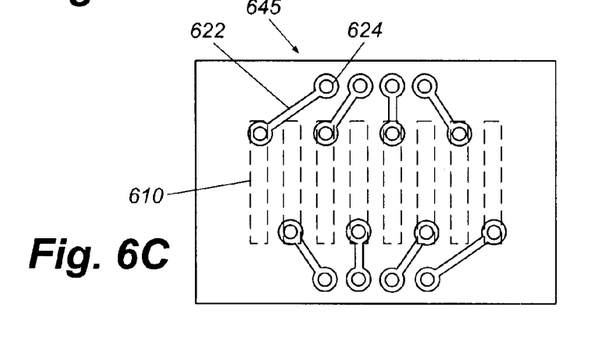
FIG. 6C is a plan view illustrating a redistribution layer including the transducer array footprint of FIG. 6B.

FIG. 6C is a plan view illustrating an alternative embodiment of the redistribution layer 145 of FIG. 5A. The redistribution layer 645 includes the transducer array footprint 605 of FIG. 6B. Each redistribution conductor 622 connects one of the IC pads 624 to one of the pads 610 of the transducer array footprint 605. Further, in FIG. 6C, the dotted lines illustrate the outline of the transducer array footprint 605 shown in FIG. 6B. In this manner, the redistribution conductors 622 in the redistribution layer 645 make electrical connections between the IC pads 624 and each respective transducer array element 610. Accordingly, both the transducer array footprint 600 and the design of the active circuitry 618 can be independently optimized and each transducer array element 610 connected to the appropriate portion of the active circuitry 618.

Figure 7:
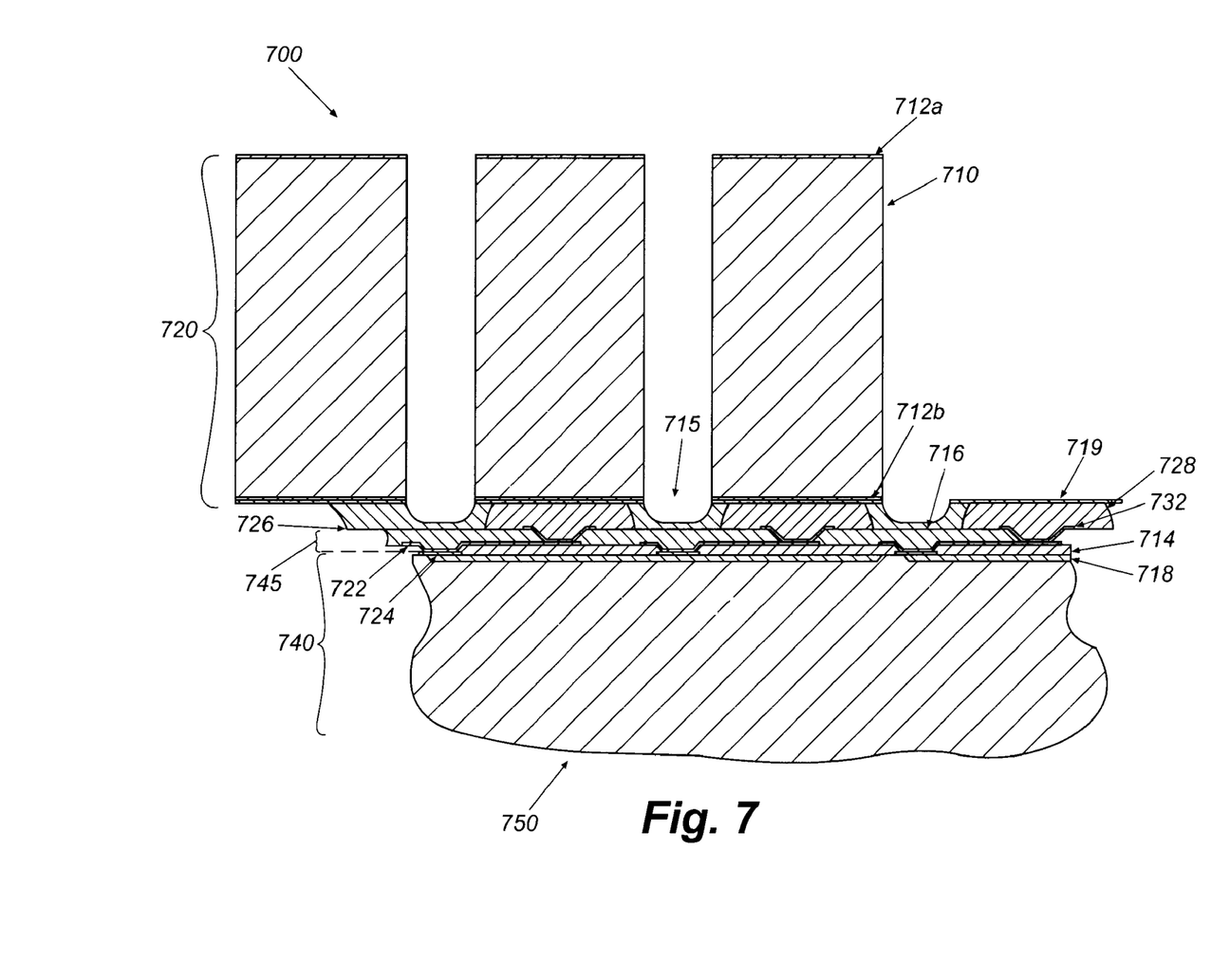
FIG. 7 is a cross-sectional schematic view illustrating an alternative embodiment of the ultrasonic transducer of FIG. 2.

FIG. 7 is a cross-sectional schematic view illustrating an alternative embodiment of the ultrasonic transducer 200 of FIG. 2. The ultrasonic transducer 700 includes an acoustic sensor 720, which comprises a plurality of piezoelectric ceramic transducer elements, an exemplar one of which is illustrated using reference numeral 710. Each piezoelectric ceramic transducer element 710 includes an element metalization layer 712a applied to the upper surface as shown. The element metalization layer 712a provides an electrical ground connection for each element 710. The ground connection typically includes a conductor (not shown) connecting each element 710 to a suitable electrical ground. Each piezoelectric ceramic transducer element 710 also includes an element metalization layer 712b applied to the underside of each piezoelectric ceramic transducer element 710 as shown. In the embodiment shown in FIG. 7, each conductive element 728 is a conductive polymer bump that is lapped flat, or planarized, as illustrated, and then metalized with a metalization layer 715. The adhesive layer 726 is also planarized and metalized. Each conductive element 728 is located over a respective metal contact 732. The element metalization layer 712b on the underside of each piezoelectric ceramic transducer element 710 is thin-line bonded to the metalization layer 715 applied over each conductive element 728.

The redistribution layer 745 includes the redistribution conductors 722 and a secondary passivation layer 716, which is similar to the secondary passivation layer 216 described above.

Each metal contact 732 is connected through a respective redistribution conductor 722 to a respective IC pad 724. The IC pad 724 connects to the active circuitry 718 located on the IC 740. The gap between the secondary passivation layer 716 and the exposed surface of the element metalization layer 712 on the piezoelectric ceramic transducer element 710 is filled with a layer of adhesive 726. The adhesive 726 is similar to the adhesive 226 described above. As described above, the transducer elements 710 can be cut using a dicing saw stopping before the saw contacts the metalization layer 712b. The remaining material of the transducer elements 710 and the metalization layer 712b can then be removed using, for example, a laser. The resulting saw kerf 715 creates the independent transducer elements 710 and removes the electrical connection between transducer elements 710.

Figure 8A:
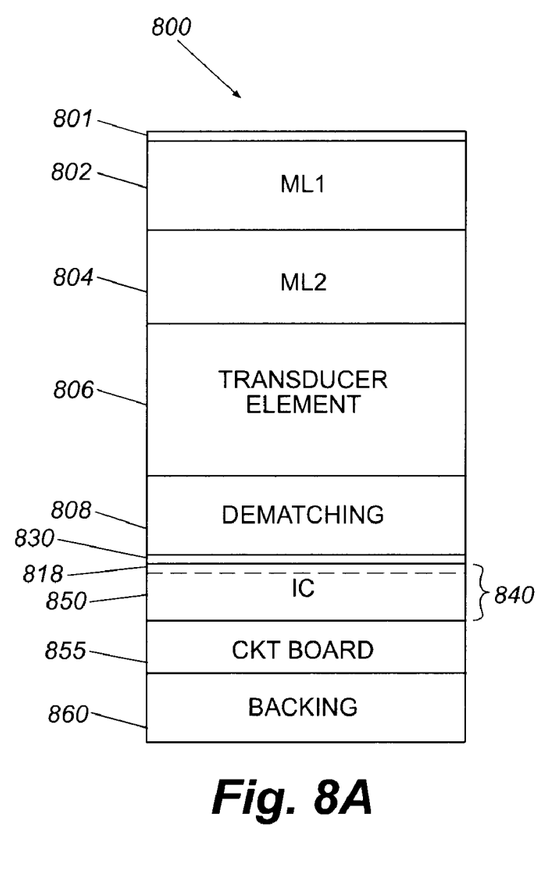
FIG. 8A is a cross-sectional schematic view illustrating one of the piezoelectric ceramic transducer elements of FIG. 2.

FIG. 8A is a cross-sectional schematic view illustrating one of the piezoelectric ceramic transducer elements of FIG. 2. The piezoelectric ceramic transducer element 800 includes a first matching layer 802 and a second matching layer 804 located over piezoelectric ceramic element 806. The matching layers 802 and 804 are electrically conductive and generally include a metalization layer 811 applied over the matching layer 802. The matching layers 802 and 804 help to match the acoustic impedance of the piezoelectric ceramic element 806 (approximately 30 megarayls (MRayls)) to the acoustic impedance of the patient (approximately 1.5 MRayls). The MRayl is a unit of measure of acoustic impedance.

For example, by using the matching layers 802 and 804, in a ¼ wave arrangement, the 1.5 MRayl acoustic impedance of the patient can be closely matched to the 30 MRayl acoustic impedance of the piezoelectric ceramic element 806. Alternatively, instead of using a pure piezoelectric ceramic element, the acoustic impedance of the piezoelectric ceramic element 806 can be altered by fabricating the element 806 using a composite piezoelectric ceramic material.

In accordance with another aspect of the invention, a layer of an electrically conductive acoustic material is bonded to the surface of the piezoelectric ceramic element 806 opposite that of the matching layer 804. In one embodiment, the electrically conductive acoustic material is a dematching layer 808 bonded to the piezoelectric ceramic element 806 as shown. The dematching layer 808 acts as an acoustic reflector and may be a high impedance dematching layer, constructed of, for example, tungsten-carbide, having a cobalt or nickel binder and having an acoustic impedance of approximately 80–100 MRayls. Alternatively, a low impedance dematching layer, constructed of, for example a polymer or polymer mixtures, such as, for example, epoxy having an acoustic impedance of approximately 3 MRayls and epoxy-metal mixtures such as epoxy-silver having an acoustic impedance of approximately 4.5 MRayls. For example, the electrically conductive dematching layer 808 might be tungsten-carbide, having acoustic impedance on the order of 80–100 MRayls. In this manner, the high impedance dematching layer 808 reflects acoustic energy back towards the piezoelectric ceramic element 806, which has an acoustic impedance of approximately 33 MRayls. The dematching layer 808 is bonded to the IC 840, which has acoustic impedance on the order of 19 MRayls. Both surfaces of the dematching layer reflect waves, as known to those having ordinary skill in the art. The small amount of energy that passes through the dematching layer 808 is transmitted into the IC substrate 850, circuit board 855 and into the backing 860 and absorbed. Both the circuit board 855 and the backing 860 match the acoustic impedance of the IC substrate 850.

As known to those having ordinary skill in the art, other than the interface 830, which is similar to the interface 130 described above, all elements in FIG. 8A are attached using acoustic bonds. The IC 840 is similar to the IC 140 described above and can be joined to the dematching layer 808 through interface 830, which is similar to interface 130 described above.

Alternatively, the electrically conductive dematching layer 808 might be a layer of epoxy-silver having acoustic impedance on the order of 4.5 MRayls. In this embodiment, the low impedance dematching layer 808 reflects acoustic energy back towards the piezoelectric ceramic element 806 that has an acoustic impedance of approximately 33 MRayls. The dematching layer 808 is bonded to the IC 840, which has acoustic impedance on the order of 19 MRayls. Both surfaces of the dematching layer reflect waves as known to those skilled in the art. The small amount of energy that passes through the dematching layer 808 is transmitted into the IC substrate 850, circuit board 855 and into the backing 860 and absorbed. Both the circuit board 855 and the backing 860 match the acoustic impedance of the IC substrate 850. As known to those having ordinary skill in the art, additional dematching layers can be added in alternating acoustic impedances to decrease the acoustic energy transmitted through the IC 840, circuit board 855 and into the backing 860.

Figure 8B:
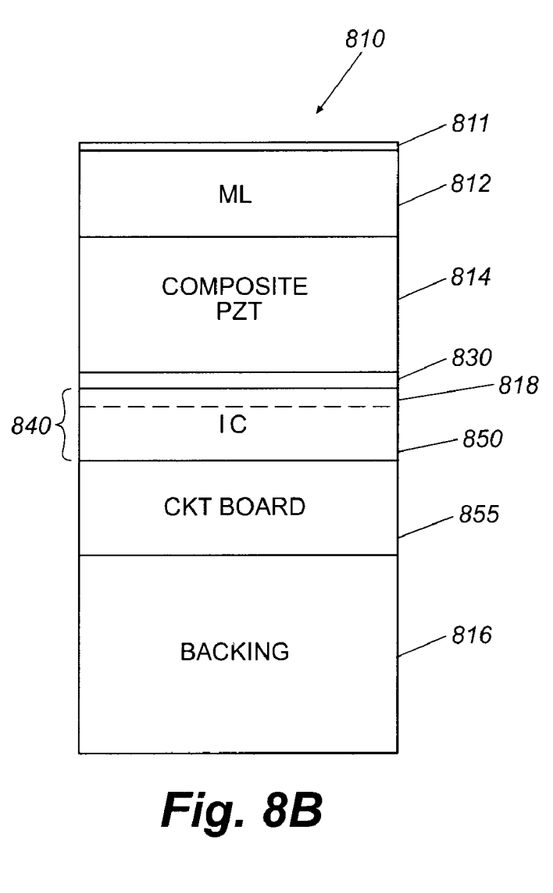
FIG. 8B is a cross-sectional schematic view illustrating an alternative embodiment of the piezoelectric ceramic transducer element of FIG. 8A.

FIG. 8B is a cross-sectional schematic view illustrating an alternative embodiment of the piezoelectric ceramic transducer element 800 of FIG. 8A. The transducer element 810 includes one matching layer 812, over which is applied metalization layer 811. The matching layer 812 is applied over the piezoelectric ceramic element 814, which has acoustic impedance of approximately 33 Mrayls. The acoustic impedance of the piezoelectric ceramic element 814 is closely matched to the acoustic impedance of the IC substrate 850. This configuration may be desirable in some cases because it can provide a larger operating bandwidth. The transducer element 810 could also be constructed using a composite polymer and piezoelectric ceramic element 814, which has acoustic impedance matched to the acoustic impedance of the IC substrate 850.

Another configuration is to place the transducer element on a backing having conductors over the redistribution layer on the IC. Such a backing including conductors is described in commonly assigned U.S. Pat. No. 5,267,221, entitled "BACKING FOR ACOUSTIC TRANSDUCER ARRAY" to Miller et al.

As known to those having ordinary skill in the art, other than the interface 830, which is similar to the interface 130 described above, all elements in FIG. 8B are attached using acoustic bonds.

In this embodiment, the electrically conductive acoustic layer applied to the circuit board 855 is a backing layer 816. The backing layer 816 acts as an acoustic absorption material, thereby absorbing any acoustic energy that travels through the IC 840 and the circuit board 855. Furthermore, the dematching layer 808 of FIG. 8A may be combined with the backing layer 816 of FIG. 8B to achieve the desired acoustic performance of the piezoelectric ceramic transducer element 800.

Figure 9:
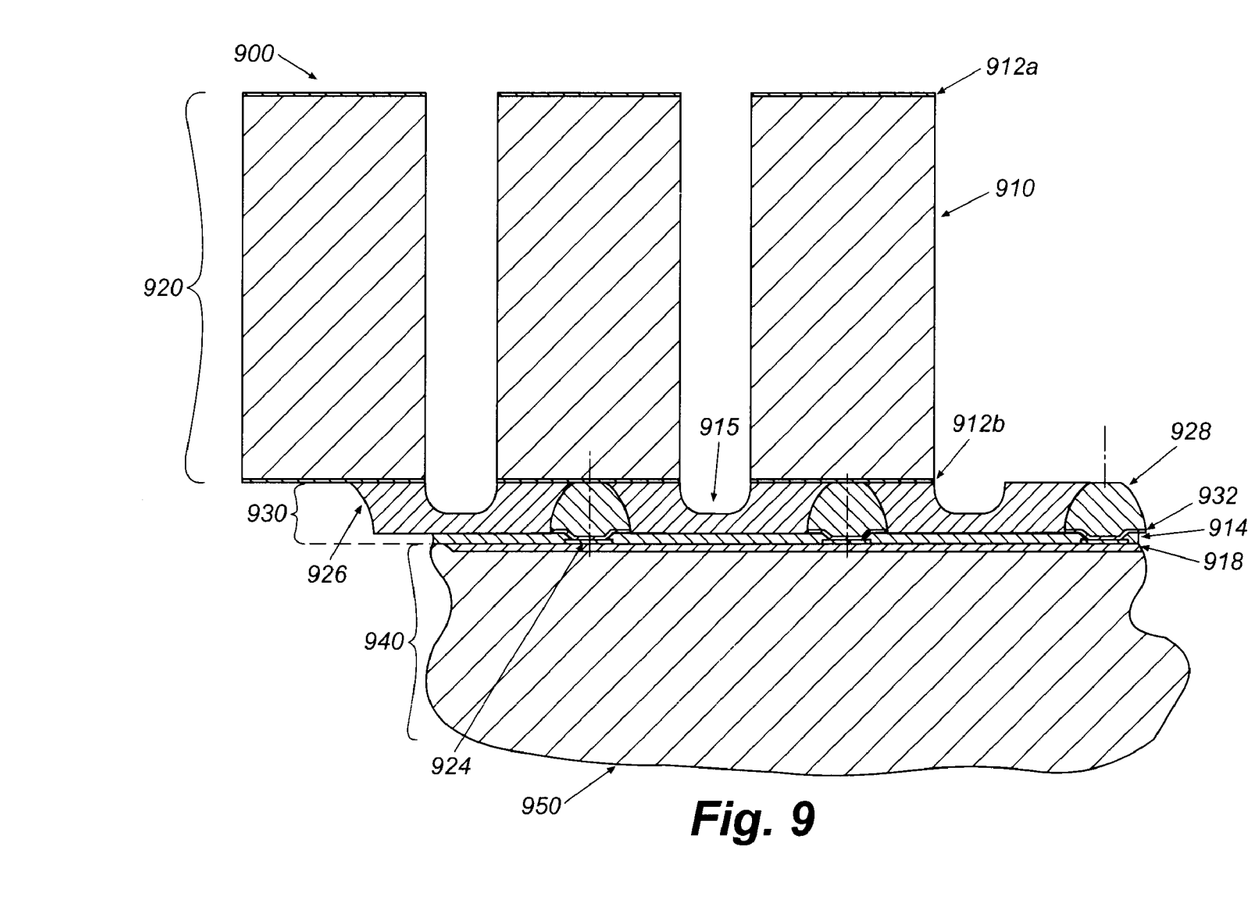
FIG. 9 is a cross-sectional schematic view illustrating another alternative embodiment of the ultrasonic transducer of FIG. 2.

FIG. 9 is a cross-sectional schematic view illustrating another alternative embodiment 900 of the ultrasonic transducer 200 of FIG. 2. The ultrasonic transducer 900 includes an acoustic sensor 920 that, in this embodiment, comprises a plurality of piezoelectric ceramic transducer elements, an exemplar one of which is illustrated using reference numeral 910. A plurality of piezoelectric ceramic transducer elements 910 are arranged in an array, which typically includes many hundreds or thousands of individual transducer elements, and in a preferred embodiment, includes 2500 elements. Each piezoelectric ceramic transducer element 910 includes an element metalization layer 912a applied to the upper surface as shown. The element metalization layer 912a provides an electrical ground connection for each element 910. The ground connection typically includes a conductor (not shown) connecting each element 910 to a suitable electrical ground. In accordance with an aspect of the invention, each piezoelectric ceramic transducer element 910 is joined to the active circuitry 918 associated with IC 940 through a die passivation layer 914 in which the metal contacts 932 are connected directly to the IC pads 924, thereby eliminating the redistribution conductors referred to above. The die passivation layer 914 can be applied over the active circuitry 918 and IC pads, an exemplar one of which is illustrated using reference numeral 924. The die passivation later 914, can be formed using, for example, silicon dioxide or polymer.

Each IC pad 924 is in electrical contact with a corresponding portion of the active circuitry 918 and the underside of metal contact 932. As illustrated in FIG. 9, the redistribution conductors and the secondary passivation layer referred to above are omitted because the transducer elements 910 are each aligned over corresponding IC pads 924.

In one embodiment, each piezoelectric ceramic transducer element 910 is joined to a respective metal contact 932 using a conductive element 928. The conductive element 928 can be, for example, a solder bump that forms an electrical contact between the metal contact 932 and an element metalization layer 912b applied to the underside of each piezoelectric ceramic transducer element 910. In this manner, electrical contact between the piezoelectric ceramic transducer element 910 and the active circuitry 918 is achieved. Although illustrated in FIG. 9 using solder bumps as the conductive element 928, the variety of other techniques mentioned above with respect to FIG. 2 are available for electrically connecting the metal contact 932 to the element metalization layer 912b of each piezoelectric ceramic transducer element 910.

Adhesive material 926 fills the gaps between each conductive element 928 and the space between each piezoelectric ceramic transducer element 910 and the die passivation layer 914. The adhesive 926 is typically non-conductive and can be a variety of adhesives such as, for example but not limited to, epoxy.

The ultrasonic transducer 900 is typically constructed by forming the die passivation layer 914 and the metal contacts 932 over the active circuitry 918 of the IC 940. The conductive elements 928 are then deposited over the metal contacts 932. The adhesive 926 is then deposited and the material from which the transducer elements 910 are formed is bonded to the die passivation layer 914, resulting in an electrical connection between the element metalization layer 912b and the conductive elements 928. The transducer elements 910 are then formed by removing a portion of the material that forms the transducer elements 910 and the element metalization layers 912a and 912b by, for example, cutting and lasing as described above.

Figure 10:
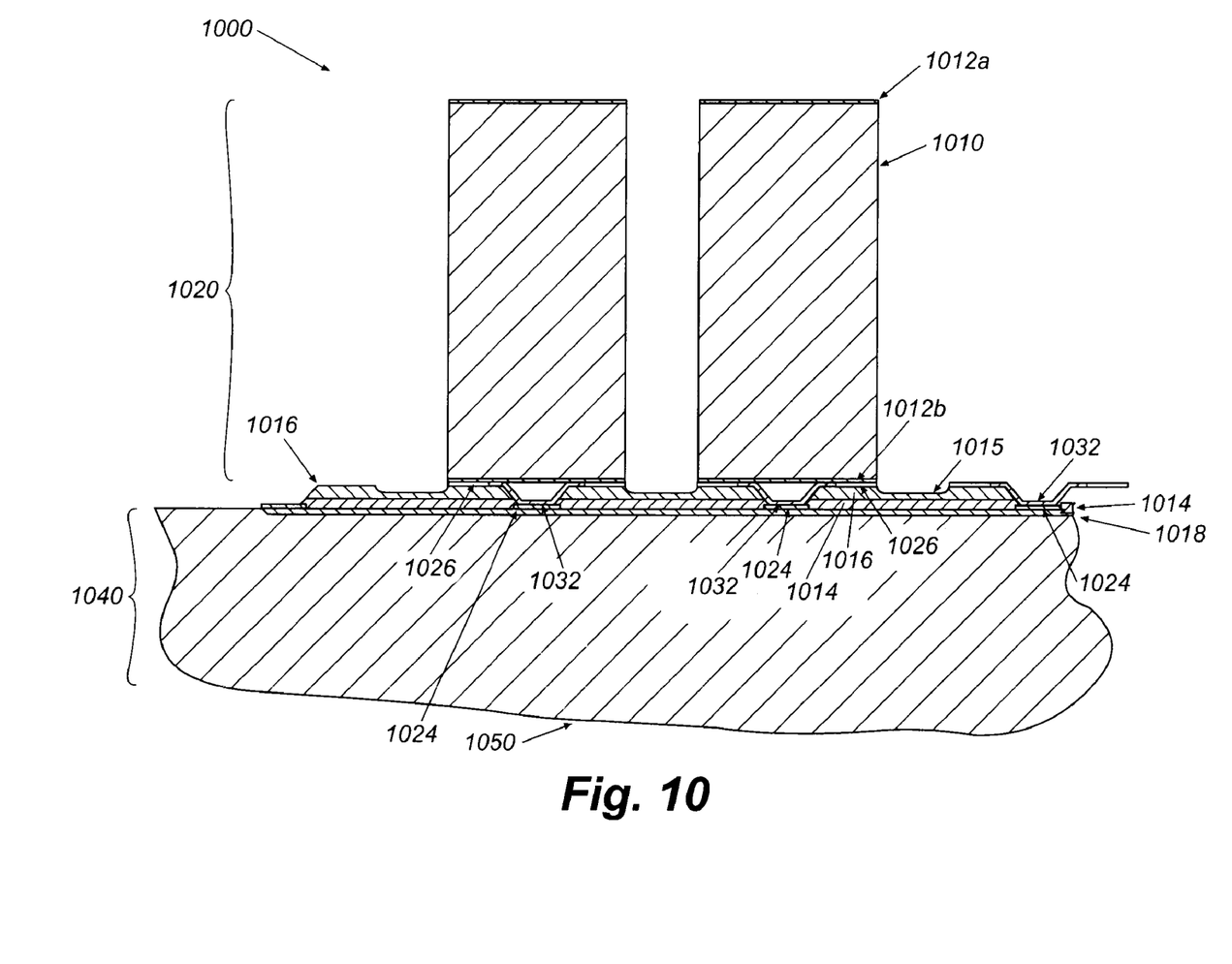
FIG. 10 is a cross-sectional schematic view illustrating an alternative embodiment of the ultrasonic transducer of FIG. 4.

FIG. 10 is a cross-sectional schematic view illustrating an alternative embodiment 1000 of the ultrasonic transducer 400 of FIG. 4. The ultrasonic transducer 1000 of FIG. 10 includes acoustic sensor 1020, which in this example includes a plurality of piezoelectric ceramic transducer elements, an exemplar one of which is illustrated using reference numeral 1010. Each piezoelectric ceramic transducer element 1010 includes an element metalization layer 1012a applied to the upper surface as shown. The element metalization layer 1012a provides an electrical ground connection for each element 1010. The ground connection typically includes a conductor (not shown) connecting each element 1010 to a suitable electrical ground. Each piezoelectric ceramic transducer element 1010 also includes an element metalization layer 1012b applied to the underside as shown. The element metalization layer 1012b allows direct electrical contact to be made between the piezoelectric ceramic transducer element 1010 and the metal contact 1032. As mentioned above, such a connection is typically referred to as a "thin-line bond." The thin-line bond electrically connects the metal contact 1032 directly to the exposed surface of the element metalization layer 1012b of the piezoelectric ceramic transducer element 1010, typically using an adhesive polymer. The thin-line bond is achieved because of the microscopic surface roughness that exists on the exposed surface of the element metalization layer 1012b and the metal contact 1032. This microscopic surface roughness provides a direct ohmic connection between the metal contact 1032 and the element metalization layer 1012b.

The metal contact 1032 connects directly to the IC bond pad 1024 without the use of the redistribution conductor described above. The IC pad 1024 connects to the active circuitry 1018 located on the IC 1040. The surface of the secondary passivation layer 1016 and a portion of the metal contact 1032 is lapped, or planarized, and metalized to level the surface of the IC 1040 and to provide an even surface over which to attach the transducer elements 1010.

The ultrasonic transducer 1000 is typically constructed by forming the IC bond pads 1024 directly over portions of the active circuitry 1018. The metal contacts 1032 are then formed over the IC bond pads 1024, and the die passivation layer 1014 and the secondary passivation layer 1016 are then formed over the active circuitry 1018 and the IC pads 1024 of the IC 1040. The exposed surface of the secondary passivation layer 1016 and portions of the metal contacts 1032 are then lapped, or planarized, flat and metalized. The element metalization layer 1012b is then thin-line bonded to the planarized surface of the secondary passivation layer 1016, resulting in a thin-line bond electrical connection between the element metalization layer 1012b and the metal contacts 1032. The transducer elements 1010 are then formed by removing a portion of the material that forms the transducer elements 1010 and the element metalization layers 1012a and 1012b by, for example, cutting and lasing as described above.

It will be apparent to those skilled in the art that many modifications and variations may be made to the present invention, as set forth above, without departing substantially from the principles of the present invention. For example, the present invention can be used with piezoelectric ceramic and MUT transducer elements. All such modifications and variations are intended to be included herein.

What is claimed is:

1. An ultrasonic transducer probe, comprising:
 a probe housing;
 an ultrasonic sensor located in the probe housing and having a plurality of elements;
 an integrated circuit located in the probe housing; and
 a redistribution layer between the ultrasonic sensor and the integrated circuit, the redistribution layer having a first surface including circuitry corresponding to the integrated circuit and a second surface including circuitry corresponding to the plurality of elements of the ultrasonic sensor.

2. The transducer probe of claim 1, wherein the ultrasonic sensor comprises a piezoelectric element.

3. The transducer probe of claim 1, wherein the ultrasonic sensor comprises a micro-machined ultrasonic transducer (MUT).

4. The transducer probe of claim 3, wherein the MUT further includes an electrically conductive via associated with each of a plurality of MUT elements, the electrically conductive via configured to provide an electrical connection between the MUT element and the second surface of the redistribution layer.

5. The transducer probe of claim 1, wherein the ultrasonic sensor and the redistribution layer are configured as a one-dimensional array.

6. The transducer probe of claim 1, wherein the ultrasonic sensor and the redistribution layer are configured as a two-dimensional array.

7. The transducer probe of claim 1, wherein the redistribution layer joins to the ultrasonic sensor using solder bumps.

8. The transducer probe of claim 1, wherein the redistribution layer joins to the ultrasonic sensor using gold bumps.

9. The transducer probe of claim 1, wherein the redistribution layer joins to the ultrasonic sensor using conductive adhesive polymer bumps.

10. The transducer probe of claim 1, wherein the redistribution layer joins to the ultrasonic sensor using adhesive polymer thin-line bonding.

11. The transducer probe of claim 1, wherein the ultrasonic probe is a transesophageal (TEE) probe.

12. The transducer probe of claim 1, further comprising an adhesive material located between the ultrasonic sensor and the redistribution layer, where the adhesive material is a dematching layer.

13. An ultrasonic transducer probe, comprising:
 an ultrasonic sensor having a plurality of elements, each element including an electrically conductive acoustic layer;
 an integrated circuit; and
 a redistribution layer between the ultrasonic sensor and the integrated circuit, the redistribution layer having a first surface having circuitry corresponding to the integrated circuit and a second surface having circuitry corresponding to the plurality of ultrasonic sensor elements.

14. The transducer probe of claim 13, wherein the electrically conductive acoustic layer is a backing layer.

15. The transducer probe of claim 13, wherein the electrically conductive acoustic layer is a dematching layer.

16. The transducer probe of claim 15, wherein the dematching layer provides low acoustic impedance.

17. The transducer probe of claim 16, wherein the dematching layer is constructed using material chosen from the group consisting of epoxy, epoxy-metal mixtures and epoxy-silver.

18. The transducer probe of claim 15, wherein the dematching layer provides high acoustic impedance.

19. The transducer probe of claim 18, wherein the dematching layer is constructed using tungsten-carbide.

20. The transducer probe of claim 13, wherein the ultrasonic sensor comprises a piezoelectric element.

21. The transducer probe of claim 13, wherein the ultrasonic sensor comprises a micro-machined ultrasonic transducer (MUT).

22. The transducer probe of claim 13, wherein the ultrasonic probe is a transesophageal (TEE) probe.

23. An ultrasonic transducer probe, comprising:
a probe housing;
an ultrasonic sensor located in the probe housing and having a plurality of elements; and
an integrated circuit located in the probe housing, wherein the ultrasonic sensor and the integrated circuit are joined using a thin-line bond.

24. The transducer probe of claim 23, wherein the ultrasonic sensor comprises a piezoelectric element.

25. The transducer probe of claim 23, wherein the ultrasonic sensor comprises a micro-machined ultrasonic transducer (MUT).

26. The transducer probe of claim 23, wherein the ultrasonic probe is a transesophageal (TEE) probe.

27. The transducer probe of claim 23, further comprising:
a pad associated with the integrated circuit and arranged to correspond with the location of each of the plurality of elements of the ultrasonic sensor;
a conductor associated with the pad and with each of the elements of the ultrasonic sensor; and
where each conductor is joined to each of the plurality of elements of the ultrasonic sensor using an adhesive polymer thin-line bond.

28. The transducer probe of claim 27, further comprising a passivation layer applied over and exposing the conductor, where the passivation layer and the conductor are planarized to level the surface of the integrated circuit.

29. A method for constructing an ultrasonic transducer probe, the method comprising the steps of:
providing a probe housing;
providing an ultrasonic sensor in the probe housing, the ultrasonic sensor having a plurality of elements;
providing an integrated circuit in the probe housing; and
providing a redistribution layer between the ultrasonic sensor and the integrated circuit, the redistribution layer having a first surface including circuitry corresponding to the integrated circuit and a second surface including circuitry corresponding to the plurality of elements of the ultrasonic sensor.

30. The method of claim 29, wherein the ultrasonic sensor comprises a piezoelectric element.

31. The method of claim 29, wherein the ultrasonic sensor comprises a micro-machined ultrasonic transducer (MUT).

32. The method of claim 29, further comprising the step of configuring the ultrasonic sensor and the redistribution layer as a one-dimensional array.

33. The method of claim 29, further comprising the step of configuring the ultrasonic sensor and the redistribution layer as a two-dimensional array.

34. The method of claim 29, further comprising the step of joining the redistribution layer to the ultrasonic sensor using solder bumps.

35. The method of claim 29, further comprising the step of joining the redistribution layer to the ultrasonic sensor using gold bumps.

36. The method of claim 29, further comprising the step of joining the redistribution layer to the ultrasonic sensor using conductive adhesive polymer bumps.

37. The method of claim 29, further comprising the step of joining the redistribution layer to the ultrasonic sensor using adhesive polymer thin-line bonding.

38. The method of claim 29, wherein the ultrasonic probe is a transesophageal (TEE) probe.

39. An ultrasonic transducer probe, comprising:
a probe housing;
an ultrasonic sensor located in the probe housing and having a plurality of transducer elements;
an integrated circuit located in the probe housing, the integrated circuit including a plurality of electrical pads, wherein each transducer element is located directly above only one corresponding electrical pad; and
a plurality of electrical contacts, wherein each electrical contact electrically connects one transducer element with its corresponding electrical pad.

40. The transducer probe of claim 39, wherein each of the electrical contacts joins each of the plurality of transducer elements using solder bumps.

41. The transducer probe of claim 39, wherein each of the electrical contacts joins each of the plurality of transducer elements using gold bumps.

42. The transducer probe of claim 39, wherein each of the electrical contacts joins each of the plurality of transducer elements using conductive adhesive polymer bumps.

43. An ultrasonic transducer probe, comprising:
a probe housing;
an ultrasonic sensor located in the probe housing and having a plurality of elements;
an integrated circuit located in the probe housing, the integrated circuit including a plurality of electrical pads corresponding to the locations of each of the plurality of elements; and
a plurality of electrical contacts corresponding to the electrical pads, the electrical contacts being electrically attached to each of the plurality of transducer elements, wherein each of the electrical contacts joins each of the plurality of transducer elements using at least one of gold bumps and conductive adhesive polymer bumps.

44. An improvement to an ultrasonic transducer probe having an ultrasonic sensor and an integrated circuit, comprising:
a redistribution layer between the ultrasonic sensor and the integrated circuit, said redistribution layer having a first surface including circuitry corresponding to the integrated circuit and a second surface including circuitry corresponding to a plurality of elements in the ultrasonic sensor.

45. An improved method for constructing an ultrasonic transducer probe having an ultrasonic sensor and an integrated circuit, the improvement comprising the step of:
providing a redistribution layer between the ultrasonic sensor and the integrated circuit, said redistribution layer having a first surface including circuitry corresponding to the integrated circuit and a second surface including circuitry corresponding to a plurality of elements in the ultrasonic sensor.

* * * * *